United States Patent
Burkhart et al.

(10) Patent No.: US 8,663,251 B2
(45) Date of Patent: Mar. 4, 2014

(54) IN-LINE SUTURE PASSER AND METHOD OF PASSING SUTURE

(75) Inventors: Stephen S. Burkhart, San Antonio, TX (US); Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 1107 days.

(21) Appl. No.: 12/199,753

(22) Filed: Aug. 27, 2008

(65) Prior Publication Data

US 2009/0062819 A1 Mar. 5, 2009

Related U.S. Application Data

(60) Provisional application No. 60/968,267, filed on Aug. 27, 2007.

(51) Int. Cl.
*A61B 17/04* (2006.01)
(52) U.S. Cl.
USPC ............................. 606/145; 606/144; 606/148
(58) Field of Classification Search
USPC ......................................................... 606/144
See application file for complete search history.

(56) References Cited

U.S. PATENT DOCUMENTS

| | | | |
|---|---|---|---|
| 5,522,820 A * | 6/1996 | Caspari et al. | 606/148 |
| 6,551,330 B1 * | 4/2003 | Bain et al. | 606/144 |
| 6,638,283 B2 | 10/2003 | Thal | |
| 6,770,084 B1 * | 8/2004 | Bain et al. | 606/144 |
| 6,984,237 B2 * | 1/2006 | Hatch et al. | 606/144 |
| 6,997,932 B2 | 2/2006 | Dreyfuss et al. | |
| 7,879,046 B2 * | 2/2011 | Weinert et al. | 606/139 |
| 8,469,974 B2 * | 6/2013 | Skinlo et al. | 606/144 |
| 2003/0065337 A1 * | 4/2003 | Topper et al. | 606/144 |
| 2003/0078599 A1 * | 4/2003 | O'Quinn et al. | 606/144 |
| 2005/0043748 A1 * | 2/2005 | Oren et al. | 606/144 |
| 2007/0149986 A1 * | 6/2007 | Morris et al. | 606/144 |
| 2008/0208221 A1 * | 8/2008 | Murray et al. | 606/145 |
| 2013/0072948 A1 * | 3/2013 | States et al. | 606/145 |

FOREIGN PATENT DOCUMENTS

EP 0 903 109 A1 3/1999

* cited by examiner

*Primary Examiner* — Melanie Tyson
*Assistant Examiner* — Todd J Scherbel
(74) *Attorney, Agent, or Firm* — Dickstein Shapiro LLP

(57) ABSTRACT

An apparatus and method for passing suture in tissue repair and other surgical procedures. The apparatus includes a pair of jaws mounted on a distal end of a shaft, a handle assembly mounted on a proximal end of the shaft, and a needle mounted on the handle assembly and through a cannulation of the shaft. A suture is placed in a slot at the tip of the lower jaw. By advancing the needle relative to the body of the instrument, the needle is pushed forward to capture the suture and to pull it through the tissue to be sutured in a direction about parallel to the longitudinal axis of the shaft.

3 Claims, 8 Drawing Sheets

IN-LINE SUTURE PASSER AND METHOD OF PASSING SUTURE

CROSS-REFERENCE TO RELATED APPLICATIONS

This application claims the benefit of U.S. Provisional Application No. 60/968,267, filed Aug. 27, 2007, the entire disclosure of which is incorporated by reference herein.

FIELD OF THE INVENTION

The present invention relates to a surgical instrument for suturing tissue and, more particularly, to a hand-held inline suture passer used to pass suture through tissue.

BACKGROUND OF THE INVENTION

Surgical procedures require time-consuming suturing of soft tissue. Generally, suture needles with attached suture strands are grasped either manually or by forceps and passed through the desired work site so a knot can be tied. In endoscopic procedures, where access to the work site is inherently limited, surgeons must use auxiliary devices to be able to pass suture strands through desired tissue.

Various instruments and techniques have been developed for surgical repairs requiring the passing of sutures to otherwise difficult to access locations. For example, U.S. Pat. No. 6,997,932 discloses an elongated suture passer which deploys a circular suture carrier to pierce tissue. By this action, the suture is passed through the soft tissue and into a tip catch. The suture carrier disengages and the elongated suture passer can be retracted, leaving the suture intact. While suitable for joining relatively stable soft tissue, such elongated suture passers have no means for securing the surrounding tissue. Additionally, the elongated suture passer must be inserted into the work site, which is problematic if the work site is too small to accommodate such an instrument.

U.S. Pat. No. 6,638,283 to Thal discloses a surgical suture passer with opposed jaws for grasping tissue. Once the tissue is grasped, the upper jaw serves as a guide to passing the needle into the hollow lower jaw. The needle is retained in the hollow lower jaw and the device is withdrawn. While suitable for relatively accessible work sites, it is advantageous to have a single device for suturing so as not to crowd the site. Further, the needle could become disengaged from the hollow lower jaw and become lost in the work site.

Accordingly, there is a need for an improved suture passing instrument that overcomes the disadvantages of the prior art and allows a surgeon to quickly, accurately, and easily pass suture through soft tissue.

SUMMARY OF THE INVENTION

The present invention provides a suture passing instrument and technique for surgical repairs. The suture passing instrument comprises an elongated tubular member that houses a needle, and a jaw (comprising an upper jaw and a lower jaw) coupled to the distal end of the elongated tubular member. The upper jaw is substantially straight with respect to the elongated member and is integral with the elongated member. The lower jaw is pivotably connected to the upper jaw. A suture is placed in a slot at the tip of the lower jaw. By advancing the needle relative to the body of the instrument, the needle is pushed forward to capture the suture and then pull it back through the tissue to be sutured, in a direction about parallel to a longitudinal axis of the tubular member.

These and other features and advantages of the invention will become apparent from the following detailed description when read in conjunction with the accompanying drawings and illustrated exemplary embodiments of the invention.

DESCRIPTION OF THE INVENTION

Figure 1:
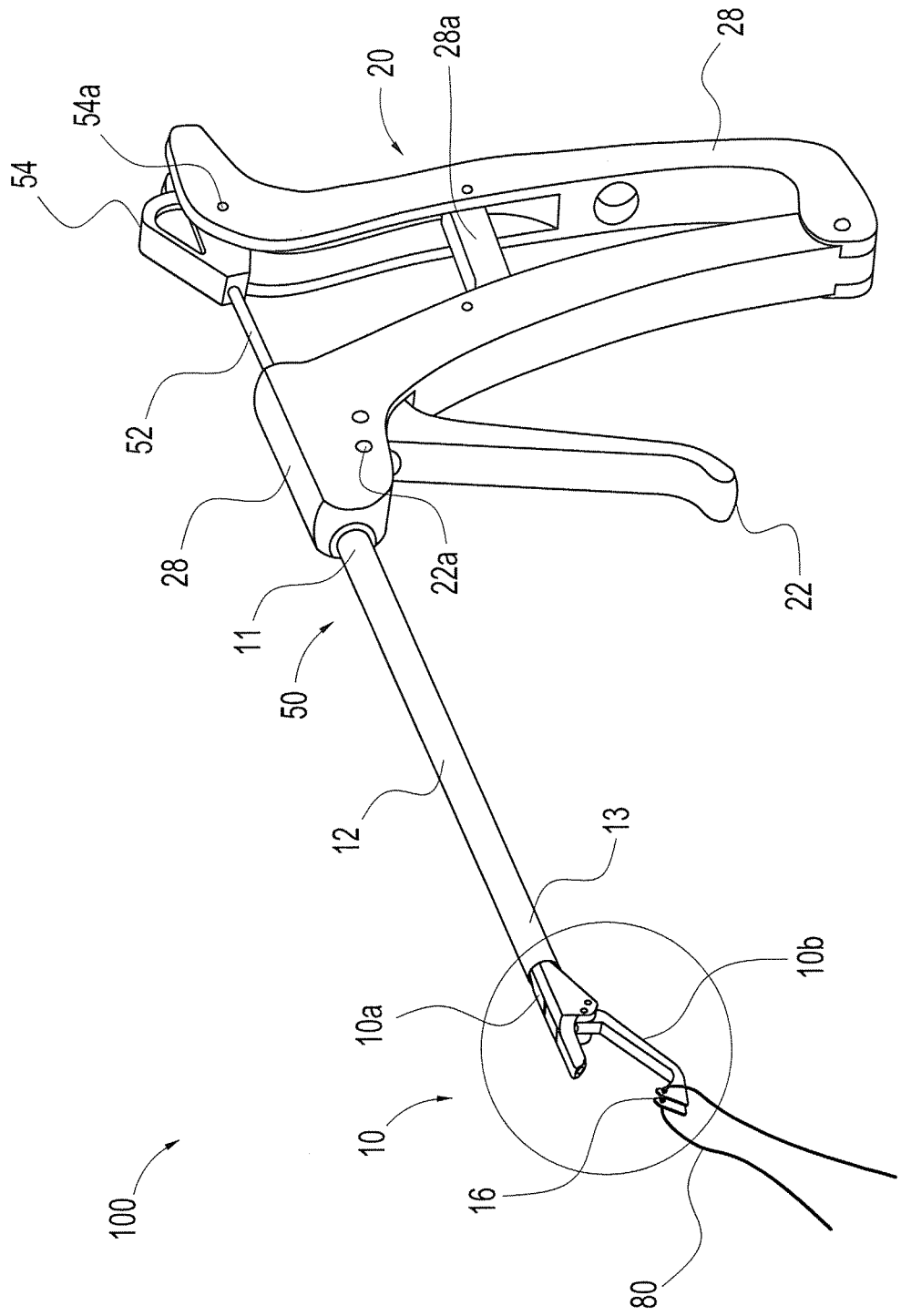
FIG. 1 is a perspective view of the suture passing instrument of the present invention.
Figure 2:
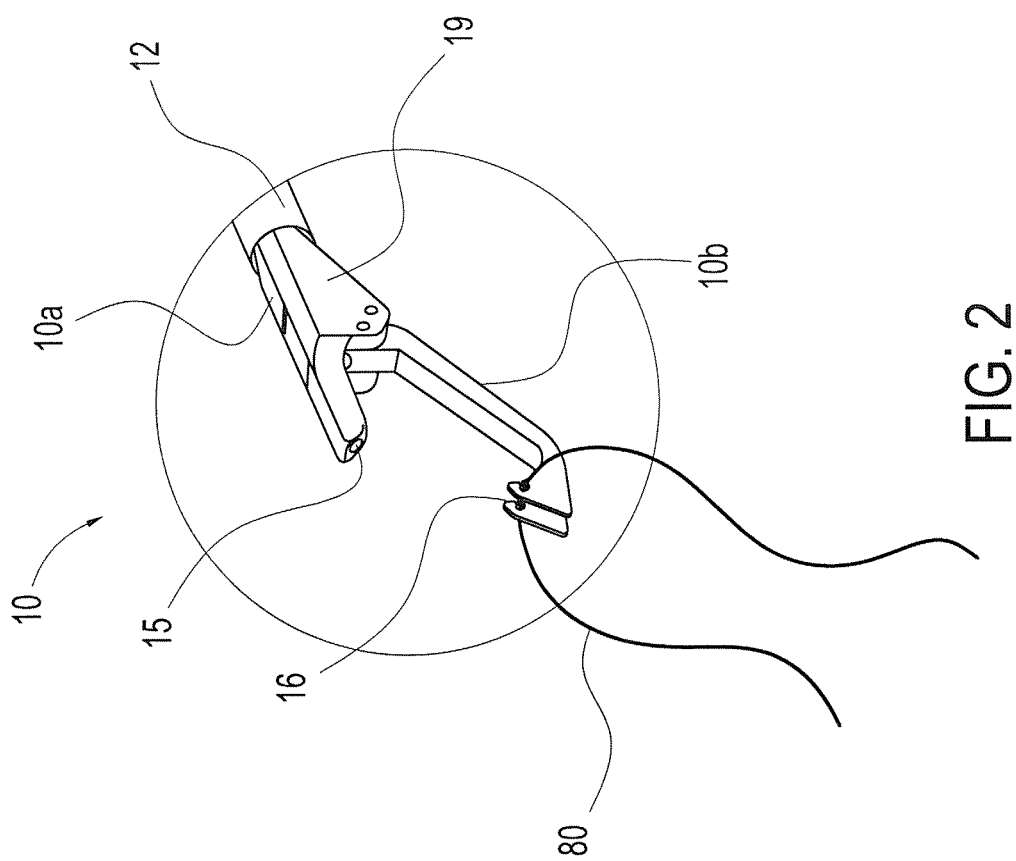
FIG. 2 is an enlarged perspective view of the end of the elongate member for housing the needle of FIG. 1 showing a suture hooked to a slot at the end of the jaw.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

The present invention provides a suture passing instrument and surgical technique for endoscopic surgical repairs. The suture passing instrument comprises an elongated tubular member that has a channel housing a needle. A handle assembly comprises a trigger mechanism and a handle, the trigger mechanism being pivotally connected to the handle. The trigger mechanism articulates a lower jaw (coupled to the tip of the elongated tubular member) relative to an upper jaw. A suture is placed in a slot at the tip of the lower jaw. By squeezing the trigger mechanism, the lower jaw is articulated relative to the elongated tubular member and to the upper jaw, thereby securing contact with the tissue. By actuating the handle, the needle is advanced relative to the body of the instrument, the needle being pushed forward to capture the suture extending within the slot in the lower jaw, and then to pull back the suture (captured in a hook of the needle) through the tissue to be sutured.

Referring now to the drawings, where like elements are designated by like reference numerals, FIGS. 1-8 illustrate various structural elements of suture passing instrument 100 of the present invention provided with needle 55 designed to engage and pass a flexible strand 80 (e.g., suture strand 80) in a linear direction about parallel to the longitudinal axis of the instrument.

FIG. 1 illustrates suture passing instrument 100 of the present invention having suture passing instrument 100 comprising an elongated tubular member or shaft 12 having a longitudinal axis 12a, a proximal end 11, a distal end 13 and an axial throughbore therein (not shown). Elongated tubular member 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity.

Elongated tubular member 12 connects a handle assembly 20 with a tip 10 consisting of a pair of jaws 10 comprising an upper jaw 10a and a lower jaw 10b. Upper jaw 10a is provided at the distal end 13 of the instrument and is preferably integral with the tubular member 12. As illustrated in FIGS. 1-8, upper jaw 10a is substantially straight with respect to the shaft, while the lower jaw 10b is designed to pivot with respect to the upper jaw 10a.

The lower jaw 10b of the suture passing instrument 100 includes a securing mechanism 16 provided at the distal end of the jaw 10b. The securing mechanisms 16 is formed integrally with the jaw and is preferably a transversal suture loading slot 16. Slot 16 is preferably arcuate, to allow suture or a strand of flexible material to extend therethrough, in a position about perpendicular to the longitudinal axis of the elongated tubular member. Slot 16 is preferably formed to dimensions smaller than those of the suture slots known in the art, to prevent unwanted sutures and tissue from inadvertently getting hooked. Slot 16 may include a transversal slot with two lateral slots, grooves or wedges, each of the lateral slots, grooves or wedges being disposed on each end of the transversal slot, to allow increased suture positioning for future suture manipulation with the needle construct of the invention.

Preferably, the securing mechanism is designed to allow secure placement of the suture strand within it, while allowing a needle to travel in a to- and fro-direction relative to the transversal suture strand. Securing mechanism 16 preferably comprises two lateral, opposing slots, each disposed on one of the two lateral sides of the lower jaw 10b. The two opposing slots are provided in the lateral sides of the lower jaw 10b so that a suture strand disposed therein is supported only by the two slots (i.e., without support from the body of the lower jaw 10b). In this manner, when needle 55 is advanced to travel toward the lower jaw, to capture the suture strand, the needle can pass past the two slots to allow capturing of the suture strand in hook 55a, and then pull back in an opposite direction (again passing past the two slots) to allow pulling of the suture strand away from the distal end of the instrument.

When disposed in the slot 16, strand of suture 80 is placed below the upper jaw 10a and above the lower jaw 10b, with the ends of the suture being pulled in a transversal direction relative to the slot such that the suture is wedged securely into the slot 16. When disposed in the slot 16, the suture is securely in place for engagement by the needle 55. The suture is preferably a braided suture such as a Fiberwire™, sold by Arthrex, Inc., Naples, Fla.

Figures 5, 5A:
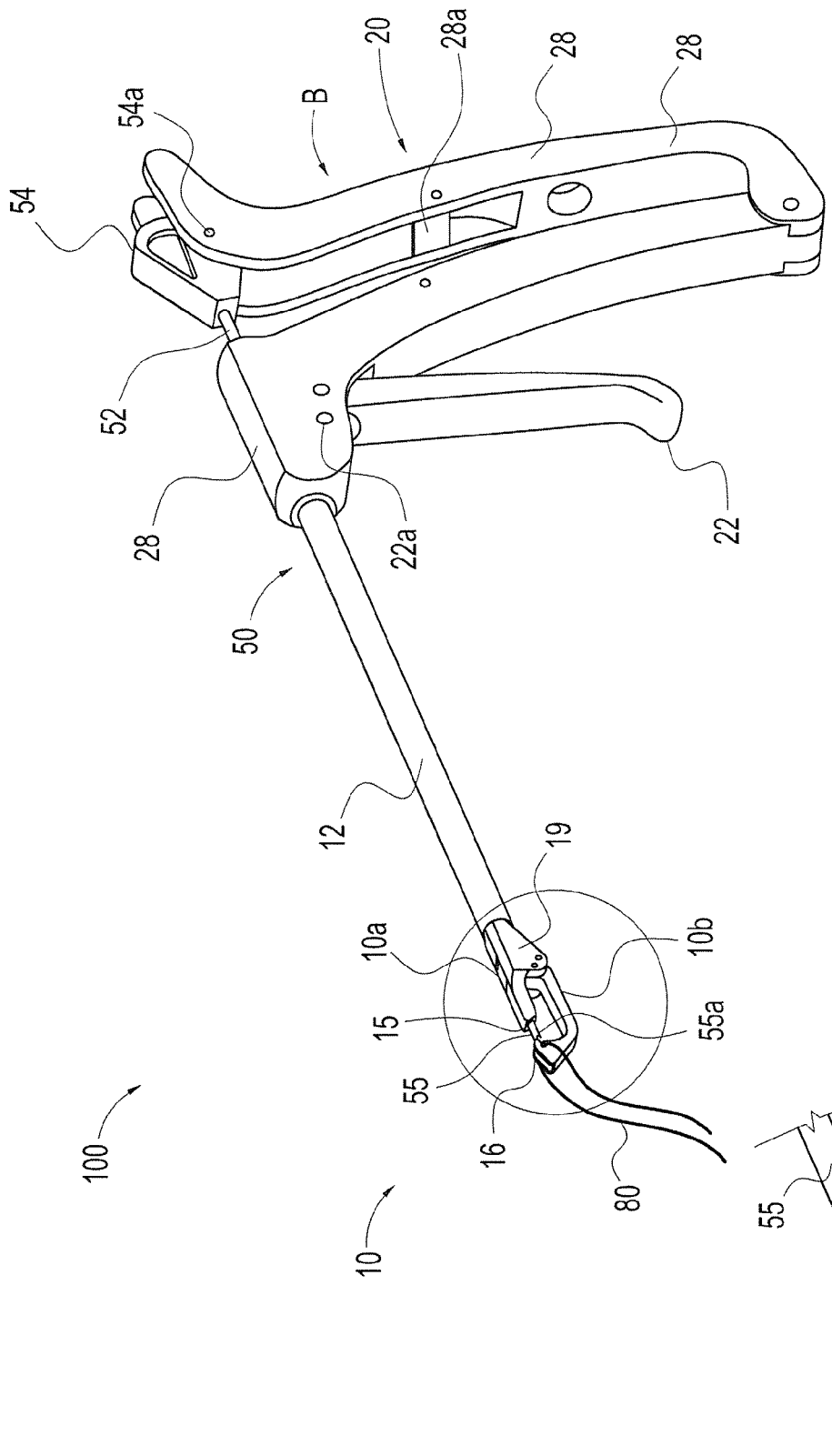
FIG. 5 is a perspective view of the suture passing instrument of the present invention, showing the action of actuating the handle of the handle assembly and the resulting action of pushing the needle forward, towards the articulated lower jaw.
FIG. 5a is an enlarged, partial cross-sectional view of the distal end of the needle of the suture passing instrument of FIG. 5.
Figure 6:
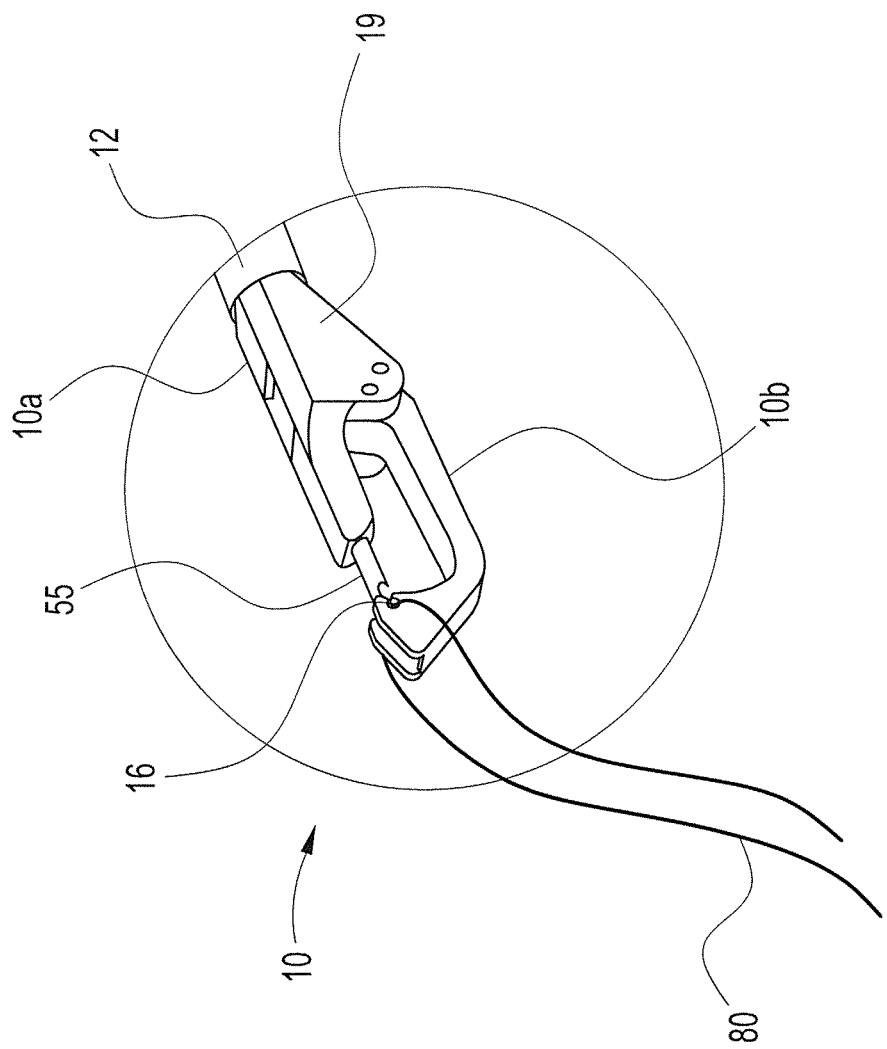
FIG. 6 is an enlarged perspective view of the end of the elongate member of the instrument of FIG. 5.

Upper jaw 10a is also provided with an openings 15 that allows needle 55 to pass and extend therethrough, as illustrated in FIGS. 5, 5a and 6, for example. Opening 15 is provided in a most distal end of upper jaw 10a. Preferably, the opening 15 has the shape of a channel with a rectangular or square cross-section to allow the needle (which may have a generally square or rectangular cross-section, or a generally circular cross-section) to pass therethrough.

Figure 7:
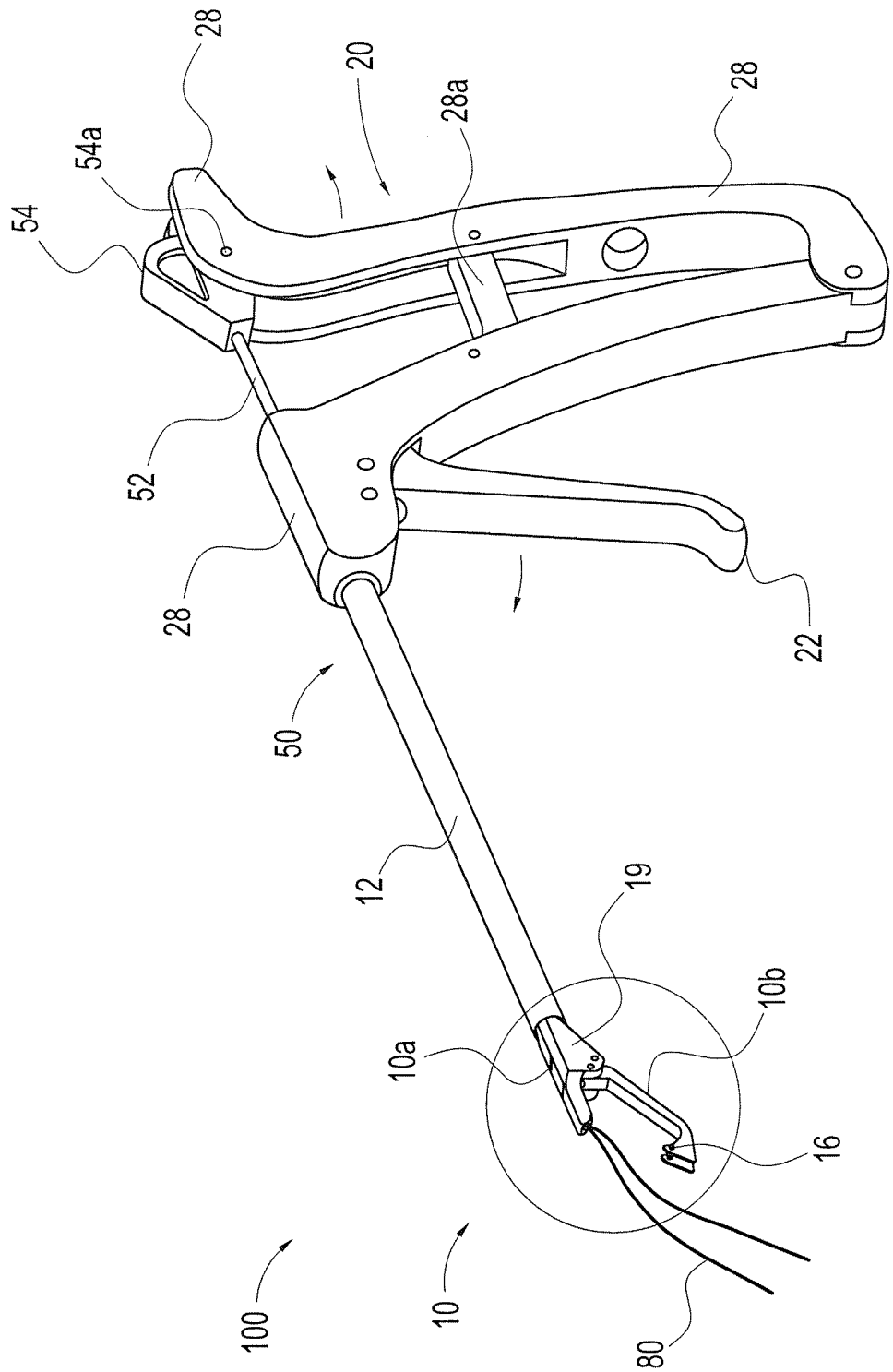
FIG. 7 is a perspective view of the suture passing instrument of the present invention, showing the action of releasing the needle actuating structure, thereby retracting the needle and suture.
Figure 8:
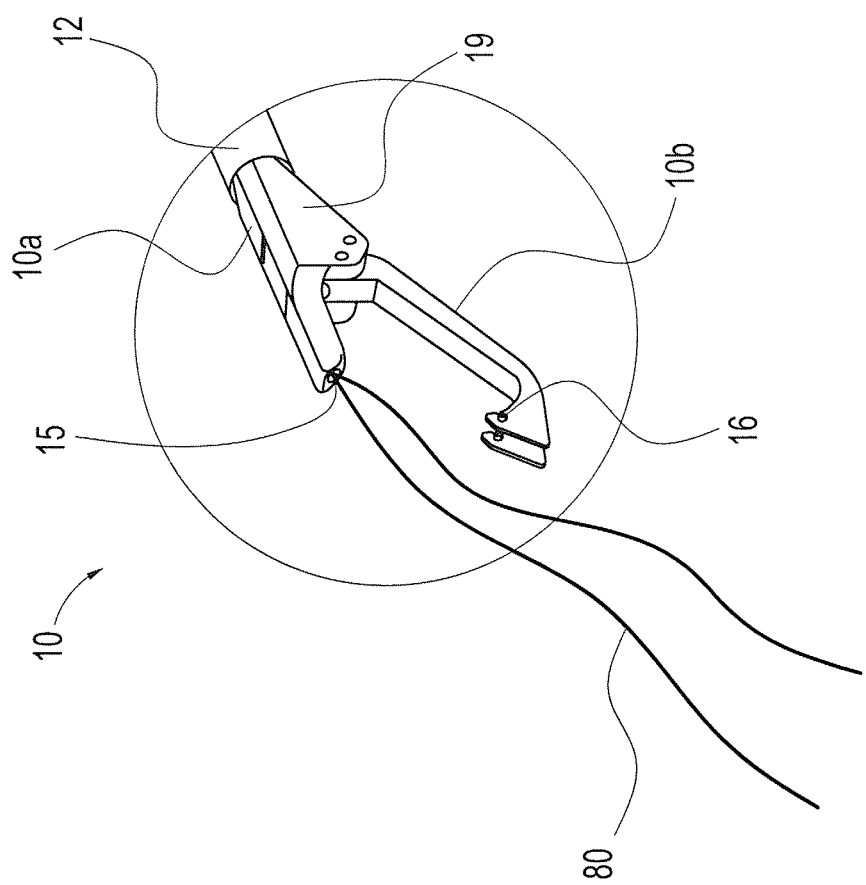
FIG. 8 is an enlarged perspective view of the distal end of the elongate member of the instrument of FIG. 7.

As shown in FIGS. 6 and 7, distal opening 15 allows needle 55 to exit in a direction about parallel to the longitudinal axis of the instrument. Preferably, needle 55 is housed in a shaft 52 which is slidingly received in the axial throughbore (channel) of the elongated tubular member 12. Needle 55 is substantially disposed within the channel of the shaft 12 when the needle is in a non-operative, or non-piercing, position. In an operative position, the needle is advanced distally to exit openings 15 in the upper jaw 10a.

Preferably, needle 55 has a narrow, pointed tip at a distal end and a hook 55a that is adjacent the pointed tip and that has an opening facing the proximal end of the instrument (FIG. 5a). The opening of hook 55a also preferably faces downwardly (i.e., in a plane extending below the longitudinal axis 12a of the device). Needle 55 may preferably be formed of nitinol or other suitable material.

Needle actuator 50 houses needle 55 and comprises shaft 52 (which is slidingly received in the axial throughbore (channel) of the elongated tubular member 12) and a most proximal end 54 provided with a slot that is engaged securely into a cross pin 54a on the proximal end of handle 28 of the suture passing instrument. The needle actuator facilitates passing the suture 80 through the tissue. In use, needle actuator 50 is actuated relative to the longitudinal axis 12a of the tubular member, and needle 55 is pushed forward toward opening 15 to exit the opening as shown in FIGS. 5 and 6, for example.

Handle assembly 20 of the suturing instrument 100 (illustrated in FIGS. 1, 3, 5 and 7) is provided at the proximal end 11 of the instrument and includes a trigger mechanism 22 (or actuating mechanism 22) and a handle 28, the trigger mechanism 22 being pivotally connected to the handle 28. The trigger mechanism 22 may consist of a finger lever 22 which, when actuated, is designed to move the lower jaw 10b relative to the upper jaw 10a. The finger lever 22 is designed to move from a first position to a second position, with a spring 22a provided to maintain tension on the finger lever 22 and to force the finger lever 22 to go back to a default position. At its default position (FIG. 1), the finger lever 22 is farthest from the distal end of the handle 28.

The suture passing instrument 100 further includes an actuator 19, which is provided within the shaft 12 and at the distal end of the shaft. A proximal end of the actuator 19 is pivotally connected to the finger lever 22 and a distal end of the actuator 19 is pivotally connected to the lower jaw 10b. The actuator 19 is designed to move the lower jaw 10b from a first position to a second position as the finger lever 22 is moved from a first position to a second position. At the default position of the finger lever 22, the lower jaw 10b is farthest from the upper jaw 10a (FIG. 1).

The proximal and distal ends of the handle 28 are linkably connected via a link 28a and tension between the proximal and distal ends may be additionally maintained using springs 28b (not shown). With hand mechanism 20, a surgeon places the device in the vicinity of tissue to be sutured (for example, two leaves of soft tissue such as tendon). By actuating the hand mechanism 20 (i.e., by bringing together the proximal and distal ends of the handle 28), pusher 54 of the needle actuator 50 advances needle 55 to capture the suture strand positioned within slot 16, and to further pull back the suture strand (captured in hook 55a of the needle) through the tissue to be sutured.

A method of employing the suture passing instrument 100 of the present invention begins by loading the needle 55 into the cannulation on the proximal end of the shaft 12 of the suture passing instrument 100. The slot on the proximal end 54 of the needle actuator 50 is engaged securely into cross pin 54a on the proximal end of handle 28 of the suture passing instrument.

Figure 3:
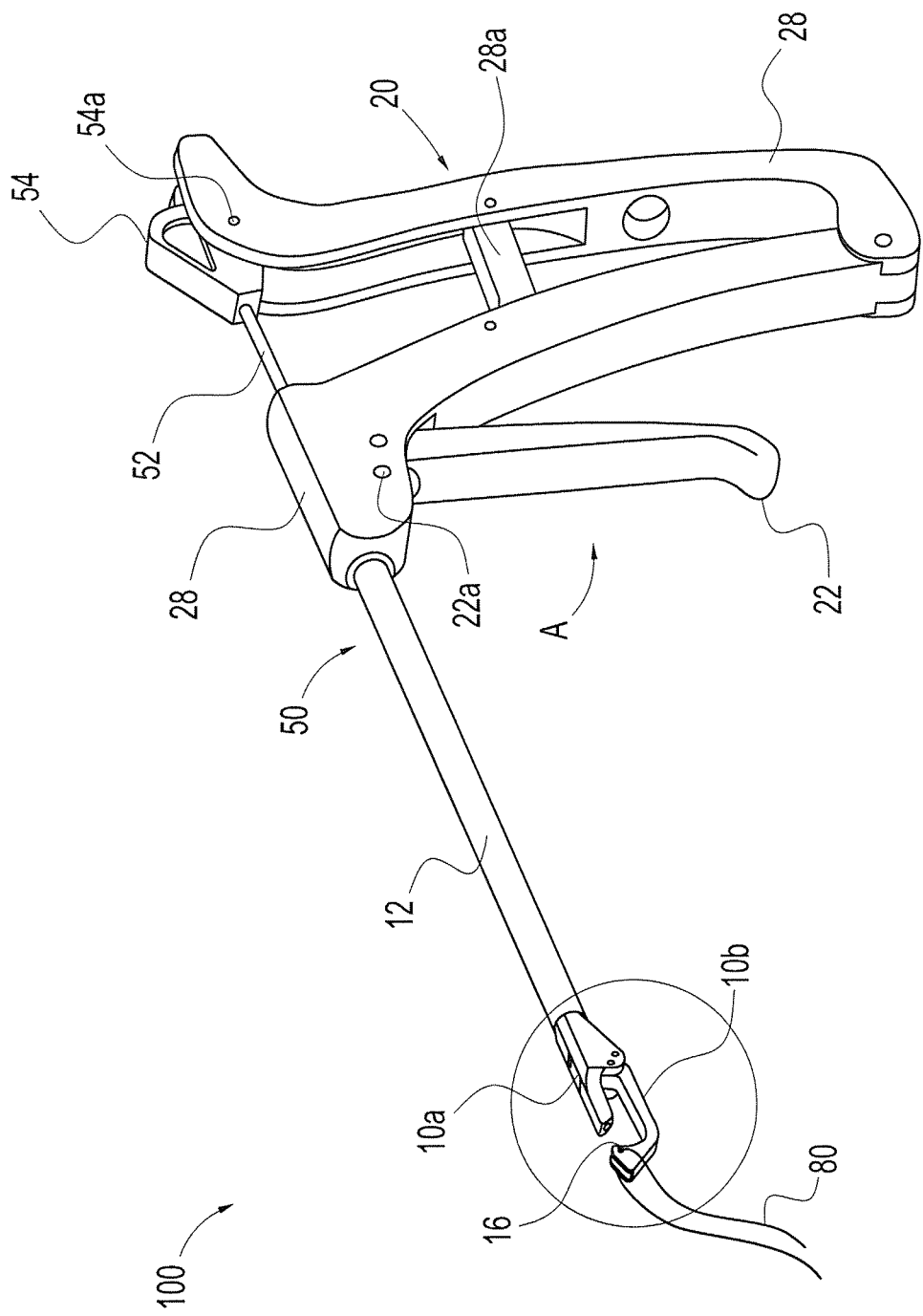
FIG. 3 is a perspective view of the suture passing instrument of the present invention, showing the action of squeezing the trigger of the handle assembly and the resulting articulation of the jaw relative to the elongate member.
Figure 4:
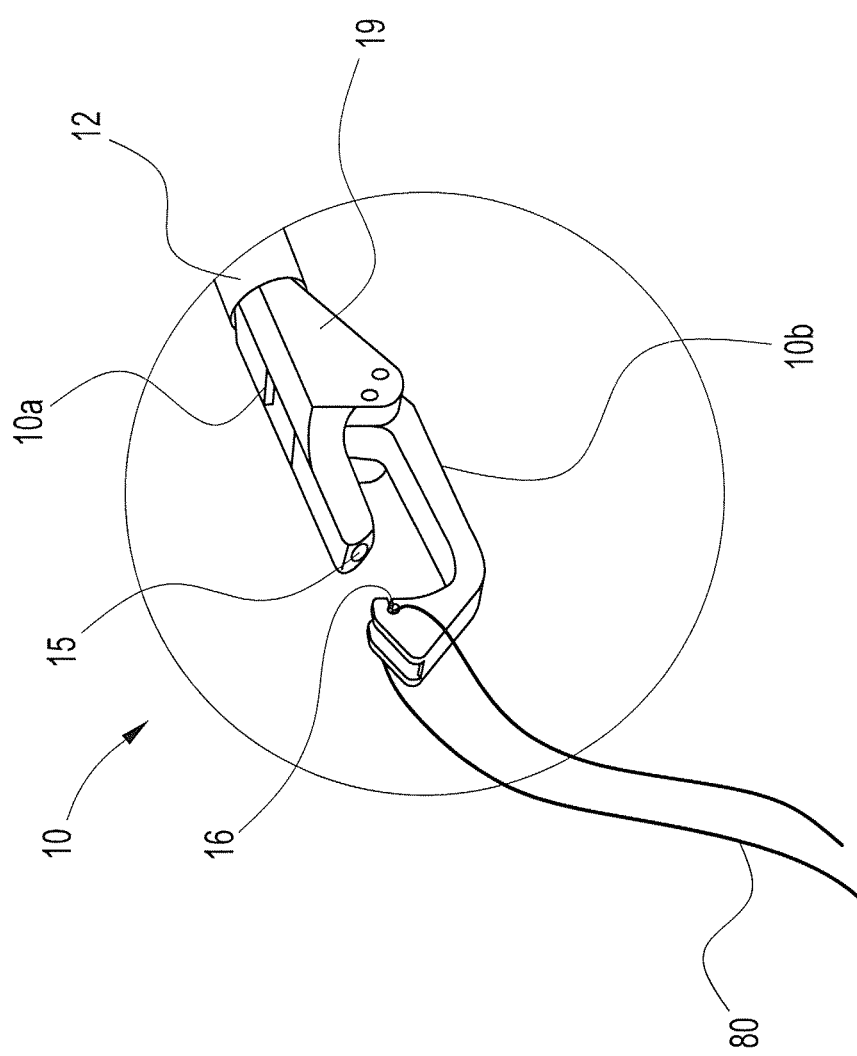
FIG. 4 is an enlarged perspective view of the end of the elongate member of the instrument of FIG. 3.

Suture 80 is loaded into the slot 16 on the lower jaw 10b of the suture passing instrument 100. Using the finger lever 22 on the suture passing instrument 100 (i.e., actuating the finger lever 22 in the direction of arrow A of FIG. 3), the upper jaw 10a and the lower jaw 10b are brought together (i.e., the lower jaw is brought in line with the upper jaw and with the longitudinal axis 12a of the device), as shown in FIGS. 3 and 4.

With the lower jaw fully raised and in line with the longitudinal axis of the device, the proximal and distal ends of handle 28 are then brought together by actuating handle 28 in the direction of arrow B (shown in FIG. 5). As a result, needle 55 is advanced distally such that the needle exits the opening 15 on the upper jaw 10a. The pointed tip of the needle 55 then pierces completely through the tissue (e.g., tendon) where the hook 55a on the needle 55 hooks the suture 80 loaded in the slot 16 of the bottom jaw. The suture is captured in hook 55a of the needle and pulled back through the soft tissue in a direction about parallel to longitudinal axis 12a of the shaft 12 of the instrument. By releasing the distal and proximal ends of handle 28, the needle 55 with the suture 80 (hooked in hook 55a of the needle 55) is pulled back through the tissue away from the lower jaw and the distal tip of the instrument, in a direction about parallel to longitudinal axis 12a. By releasing the finger lever 22, the lower jaw 10b is open (pulls away from the upper jaw 10a) and the tissue is released.

The suture passing instrument 100 of the present invention, described above with reference to FIGS. 1-8, may be employed in various surgical medical procedures for advancing the suture in the proximity of a surgical site, and for employing the suture with a cannulated instrument during such surgical procedures. For example, the suture passing instrument may be employed in endoscopic procedures. Additionally, the suture passing instrument may be utilized in other general surgical and specialty procedures that require suturing at a remote site, such as inside the body. The suture passing instrument of the present invention may be also used in repairs where suture visibility or finger access can be limited.

It will be appreciated, of course, that while the suture passing instrument may be particularly useful for performing remote procedures through access sheaths, trocars and cannulated surgical instruments, it will also find use in open surgical procedures.

In an exemplary and illustrative embodiment only, a method of suturing tissue using the suture passing instrument 100 of the present invention comprises the steps of: (i) providing a suture passing instrument 100 in the proximity of anatomical tissue to be sutured; (ii) engaging a flexible strand within a slot at the tip of a lower jaw of the suture passing instrument; (iii) capturing the suture with a needle passing through the upper jaw of the instrument and in a direction about parallel with the longitudinal axis of the instrument; and (iv) advancing the suture in a direction about parallel to the longitudinal axis of the instrument.

According to another exemplary and illustrative embodiment only, a method of suturing a tissue using the suture passing instrument 100 of the present invention comprises the steps of: (i) loading a needle onto the instrument; (ii) loading a suture into a slot provided at the tip of a lower jaw of the instrument; (iii) closing the jaws by actuating a finger lever, so that the lower jaw is brought in line with the upper jaw and with a longitudinal axis of the instrument; (iv) actuating a handle to advance the needle towards the suture loaded onto the slot of the lower jaw; (v) capturing the suture with a hook of the advanced needle; and (vi) pulling the hooked suture in a direction about parallel to the longitudinal axis of the instrument.

According to exemplary embodiments only, the suture passing instrument 100 of the present invention may be employed for passing sutures side-to-side to appose two separate leaves of soft tissue (e.g., tendon), or to pass suture from a suture anchor through soft tissue to appose soft tissue (e.g., tendon) to bone.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A method of passing suture through tissue, the method comprising the steps of:

providing a suture passing instrument in the proximity of anatomic tissue to be sutured, the suture passing instrument comprising: a shaft having a longitudinal axis, a distal end and a proximal end; a first jaw integral to the distal end of the shaft and aligned with the longitudinal axis of the shaft and comprising a channel for receiving a needle and a distal opening to allow the needle to pass therethrough; a second jaw having a longitudinal axis mounted to the distal end of the shaft and pivotally connected to the first jaw such that the second jaw is movable with respect to the first jaw, the second jaw comprising two lateral, opposing side slots configured to retain a suture thereon; and a handle assembly comprising a handle and a trigger mechanism;

loading the suture onto the two lateral, opposing side slots of the second jaw by placing the suture below the first jaw and above the second jaw, and pulling ends of the suture in a transversal direction relative to the slots so that the suture is wedged securely into the slots;

mounting the needle in the suture passing instrument by sliding the needle through a cannulation in the proximal end of the shaft such that a distal end of the needle is on the distal end of the shaft;

actuating the trigger mechanism of the handle assembly to pivot the second jaw so as to bring the longitudinal axis of the second jaw in line with the first jaw and in line with the longitudinal axis of the shaft, with the tissue to be sutured disposed between the first and second jaws;

actuating the handle of the handle assembly by pushing proximal and distal members of the handle toward each other to advance the needle such that the needle exits the distal opening on the first jaw and advances toward the second jaw, passing through the tissue and toward and in between the two lateral, opposing slots of the second jaw disposed on an opposite side of the tissue and in a direction about parallel to the longitudinal axis of the shaft, to engage a portion of the suture extending between the slots in a hook of the needle; and releasing the handle of the handle assembly to retract the needle with the hooked suture through the tissue in a direction about parallel to the longitudinal axis of the shaft, and away from the two lateral, opposing slots in the second jaw.

2. The method of claim 1, wherein the needle is a nitinol needle.

3. The method of claim 1, wherein the suture is a braided suture comprising a plurality of high strength fibers.

* * * * *